United States Patent [19]
Ruhl, Jr. et al.

[11] Patent Number: 5,357,336
[45] Date of Patent: Oct. 18, 1994

[54] METHOD AND APPARATUS FOR MULTIVARIATE CHARACTERIZATION OF OPTICAL INSTRUMENT RESPONSE

[75] Inventors: Harry D. Ruhl, Jr.; Kenneth R. Beebe, both of Midland, Mich.

[73] Assignee: The Dow Chemical Company, Midland, Mich.

[21] Appl. No.: 742,620

[22] Filed: Aug. 8, 1991

[51] Int. Cl.$^5$ .............................................. G01J 3/42
[52] U.S. Cl. .................... 356/319; 356/402
[58] Field of Search ............... 356/309, 319, 402, 346

[56] References Cited

U.S. PATENT DOCUMENTS

| | | |
|---|---|---|
| 3,373,651 | 3/1968 | Mack et al. |
| 3,422,370 | 1/1969 | Collins et al. |
| 4,092,070 | 5/1978 | Smithline |
| 4,172,663 | 10/1979 | Byer et al. ........................ 356/352 |
| 4,241,997 | 12/1980 | Chraplyvy ........................ 356/309 |
| 4,525,067 | 6/1985 | Hernandez ........................ 356/346 |
| 4,729,657 | 3/1988 | Cooper et al. ..................... 356/319 |
| 4,977,563 | 12/1991 | Nakatani .......................... 372/32 |

Primary Examiner—Vincent P. McGraw
Assistant Examiner—K. P. Hantis

[57] ABSTRACT

The system consists of a light source, a monochrometer, one or more etalons or other stable samples, a detector and a computer to store reference spectra, provide a read out indicative of the spectrum, and to change the instrument response. A transfer function is used to recharacterize the instrument's wavelength position and intensity response to match the actual spectrum with the standard spectrum. In one embodiment, the etalon is used in series with the unknown sample. A spectrum of the sample and etalon is created and is extracted from the spectrum of the sample alone to provide the actual spectrum of the instrument response to the etalon alone. The actual spectrum can then be compared to the standard spectrum and the instrument response recharacterized accordingly.

20 Claims, 9 Drawing Sheets

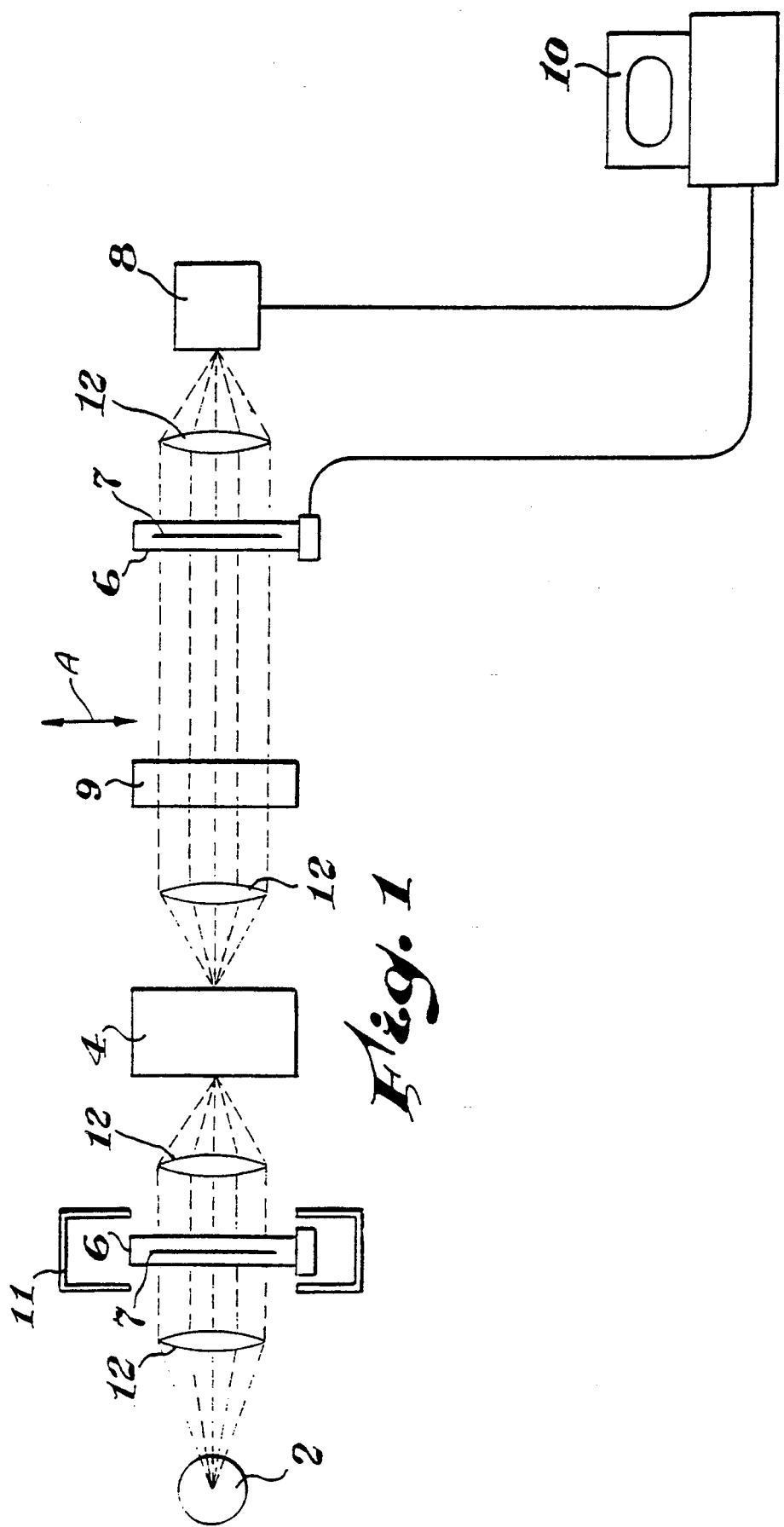

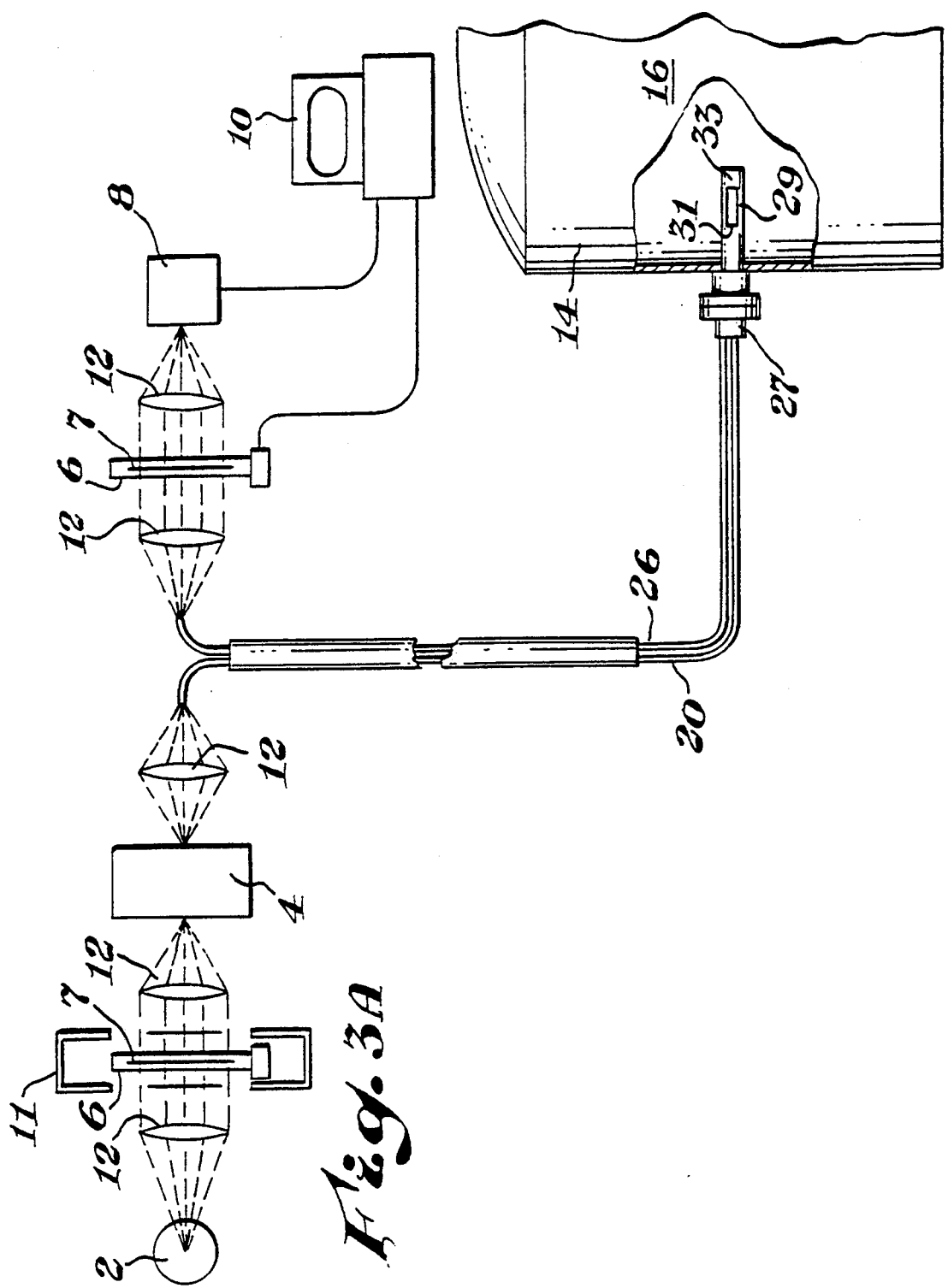

METHOD AND APPARATUS FOR MULTIVARIATE CHARACTERIZATION OF OPTICAL INSTRUMENT RESPONSE

BACKGROUND OF THE INVENTION

This invention relates, generally, to optical instruments such as spectrometers and, more particularly, to a method and apparatus for calibrating such instruments.

Optical instruments such as spectrometers use light to perform various spectral analyses. Typically, a light beam, after being filtered by a monochrometer, interferometer and Fourier transform, scanning filter photometer or the like is directed on an unknown sample to generate a resulting spectrum. The resulting spectrum can then be compared with a known spectrum to determine various characteristics of the unknown sample such as its chemical composition.

As is known in the art, it is critical that any deviations in wavelength and/or the instrument's response to light intensity be accounted for to yield accurate analytical results. If these deviations are not accounted for, the generated spectra will not be representative of the sample but will be attributable, at least in part, to these deviations. As a result, the response of the instrument will be mischaracterized and its performance will be flawed.

Various methods of recalibrating optical instruments have been developed in an attempt to account for deviations in wavelength and response to light intensity. One such recalibration method uses calibration standards that are representative of the population of unknown samples. For example, if wheat samples are to be analyzed for protein content, the calibration standards would be a set of wheat samples with known protein contents. When recalibration of the optical instrument is necessary, one or more of the known samples are reanalyzed and the resulting spectra are compared to the standard spectra from the known samples. The instrument response is then recharacterized such that the spectra from the reanalyzed standards match the original spectra for the standard samples.

One problem with such a recalibration method is that the set of calibration standards (e.g. wheat samples with known protein contents) can change and degrade over time. As a result, the sample effect will be confounded with the instrument effect such that the spectrum generated will not accurately reflect the instrument response. To avoid using degraded samples, it is possible to reanalyze the standards or prepare new standards each time the instrument is recalibrated. These approaches, however, are time consuming and introduce operator variability in reanalyzing or preparing the samples.

An alternative to the recalibration method using representative samples from the population, is to use an etalon as the known sample. Generally, an etalon consists of two parallel surfaces where both surfaces have partial reflection and partial transmission of light. For example, a solid block of germanium in air or two spaced, parallel silver plates are etalons. The only requirement is that the instrument must respond to the etalon in a way that allows for recalibration.

Examples of laser systems that utilize etalons to recalibrate instrument response can be found in U.S. Pat. No. 4,241,997 (Chraplyvy) and "Wavenumber Calibration Of Tunable Diode Lasers Using Etalons", *Applied Optics*, Vol. 17, No. 6, Mar. 15, 1978. These systems, however, disclose the use of an etalon only to recalibrate wavelength and do not address the problem of recalibrating other spectral features such as light intensity. Moreover, to use these recalibration systems, the sample must be removed. In many applications removing the sample is difficult and time consuming.

Thus, an improved method and apparatus for recalibrating optical instruments is desired.

SUMMARY OF THE INVENTION

The recalibration method and apparatus of the invention overcomes the shortcomings of the prior art by providing a system in which instrument characteristics such as light intensity can be recalibrated. The applicants have discovered the desirability and feasibility of simultaneously recalibrating an optical instrument's intensity response and wavelength position using an etalon and have developed a method for recalibrating the instrument without removing the sample from the work situs. Moreover, it has been discovered that the use of multiple etalons acting over a single region for recalibration provides improved accuracy. The system consists of a light source, a means of wavelength selection such as a monochrometer, one or more etalons or other stable samples, a detector and a processor for generating spectra and changing the instrument response. A transfer function is used to recharacterize the instrument's response to match the actual spectrum with the standard spectrum. Where the sample is not removed from the work situs, the etalon is placed in series with the unknown sample such that a combined spectrum of the sample and etalon is created. The spectrum of the sample alone is then mathematically extracted from the combined spectrum to provide the actual spectrum of the etalon alone. The actual spectrum can then be compared to the standard spectrum and the instrument response recharacterized accordingly.

BRIEF DESCRIPTION OF THE DRAWINGS

FIG. 1 shows a schematic view of one embodiment of the recalibration system of the invention.

FIGS. 3A and 3B show one example of the recalibration system used in an in situ application.

DETAILED DESCRIPTION OF THE INVENTION

Figure 2A:
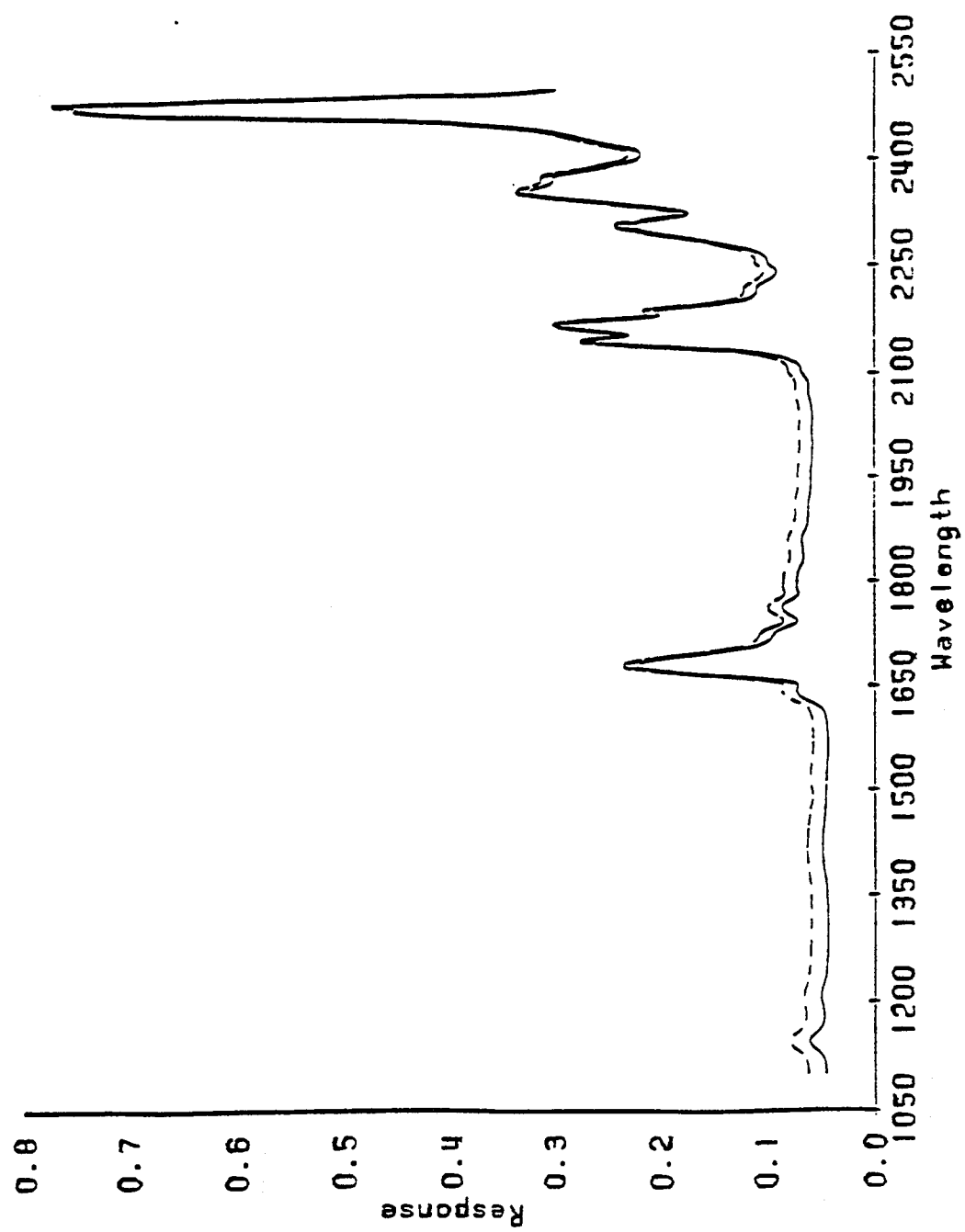
FIGS. 2A–2D are graphs of the spectra produced using the invention.

Referring more particularly to FIG. 1, the recalibration system of the invention typically includes a light source 2, a monochrometer 4 or other device for generating specific wavelengths, a support 6 for moving one or more standards 7 into the light path, and a detector 8. In the preferred embodiment, a plurality of standards 7 would be used to obtain a more accurate transfer function. The standard 7 although preferably an etalon, can also consist of neutral density filters, polymer standards such as polystyrene or any other stable standard such as glass. It is required only that the etalon standard 7 provide an instrument response that allows for instrument recalibration for the characteristic of interest. For example, if a particular intensity level of light for a particular wavelength is being analyzed, that wavelength must be within the spectral range of the etalon.

The spectrum is represented on a display, for example computer 10, where a transfer function is used to re-characterize the instrument response as will hereinafter be described. Reference spectra of the standards are stored in the computer 10. The reference spectra are used to characterize the instrument response at time of initial calibration. The computer 10 can also be used to control the position of etalon sample 7, as will hereinafter be described. Moreover, transfer optics 12 can be used if so desired.

It is contemplated that the recalibration method of the invention can be used with the sample 9 in series with the standard 7 as shown in FIG. 1 or the sample can be removed from the light path prior to recalibration as represented by arrow A. Whether or not the sample 9 and standard 7 are in series is dictated by the configuration of the system being recalibrated. When the sample 9 and standard 7 are used in series, the standard spectrum must be mathematically extracted as will be hereinafter explained with reference to FIGS. 3 and 4. Alternatively, the standard 7 can be located before the monochrometer 4 in the position shown by phantom line 11.

Figure 2B:
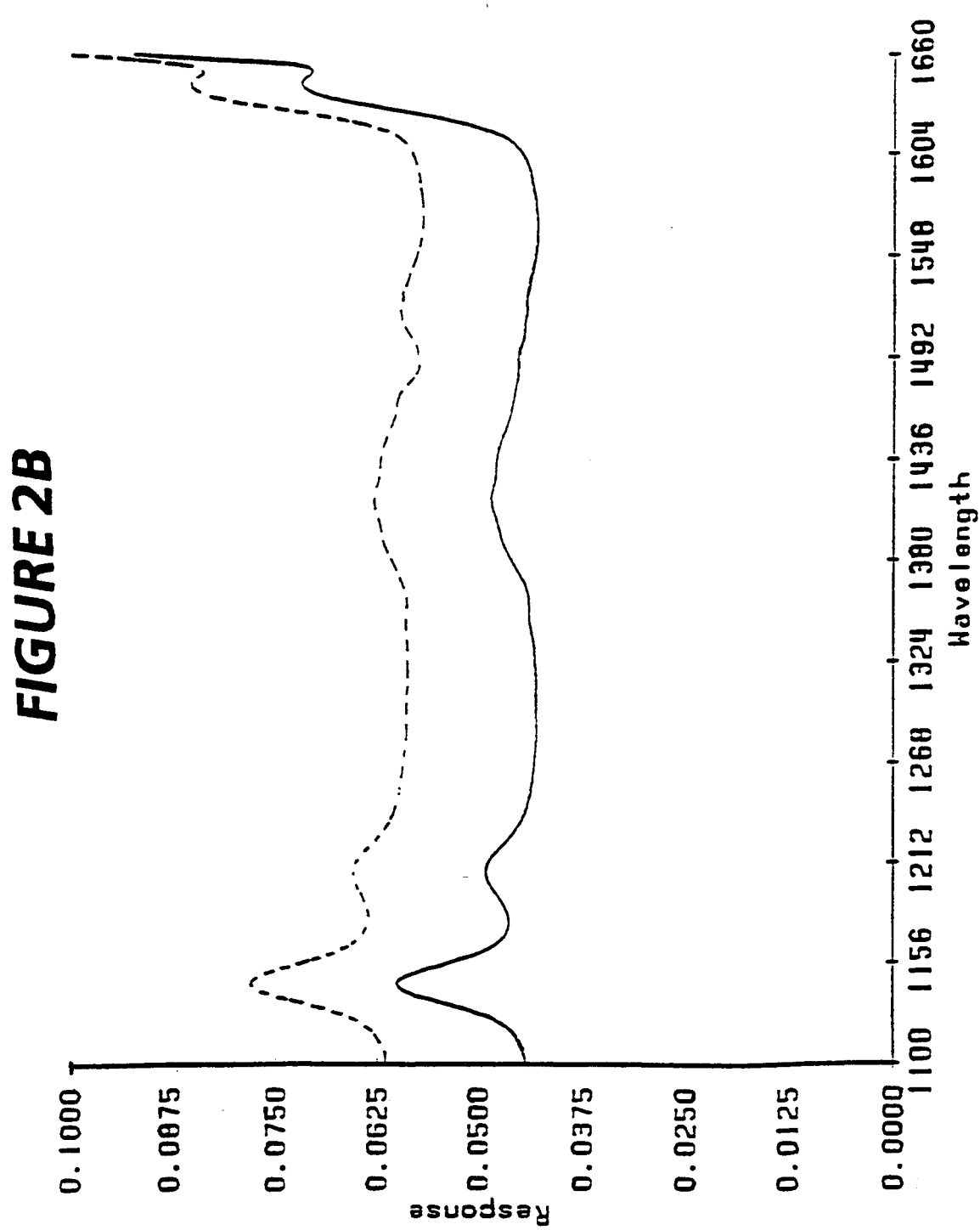

As an example of one use of the above-described system for re-calibration, polystyrene was run under two instrument conditions. FIG. 2A is a plot of the resulting spectrum of polystyrene acquired with the voltage to the source at 15.06 volts (solid lined spectra) and a spectrum acquired with the source voltage reduced to 14.625 (dashed line spectra). The voltage to the source was changed from 15.06 to 14.625 to simulate the type of change that can occur in the instrument. For illustrative purposes, the spectrum acquired at 15.06 volts is assumed to be the reference spectrum and would be stored in computer 10. As FIG. 2A indicates, the change in source voltage resulted in reduced energy throughput and a baseline offset in the resulting polystyrene spectrum. FIG. 2B is an expanded view of the region between 1100 and 1660 for the polystyrene spectrum shown in FIG. 2A.

Figure 2C:
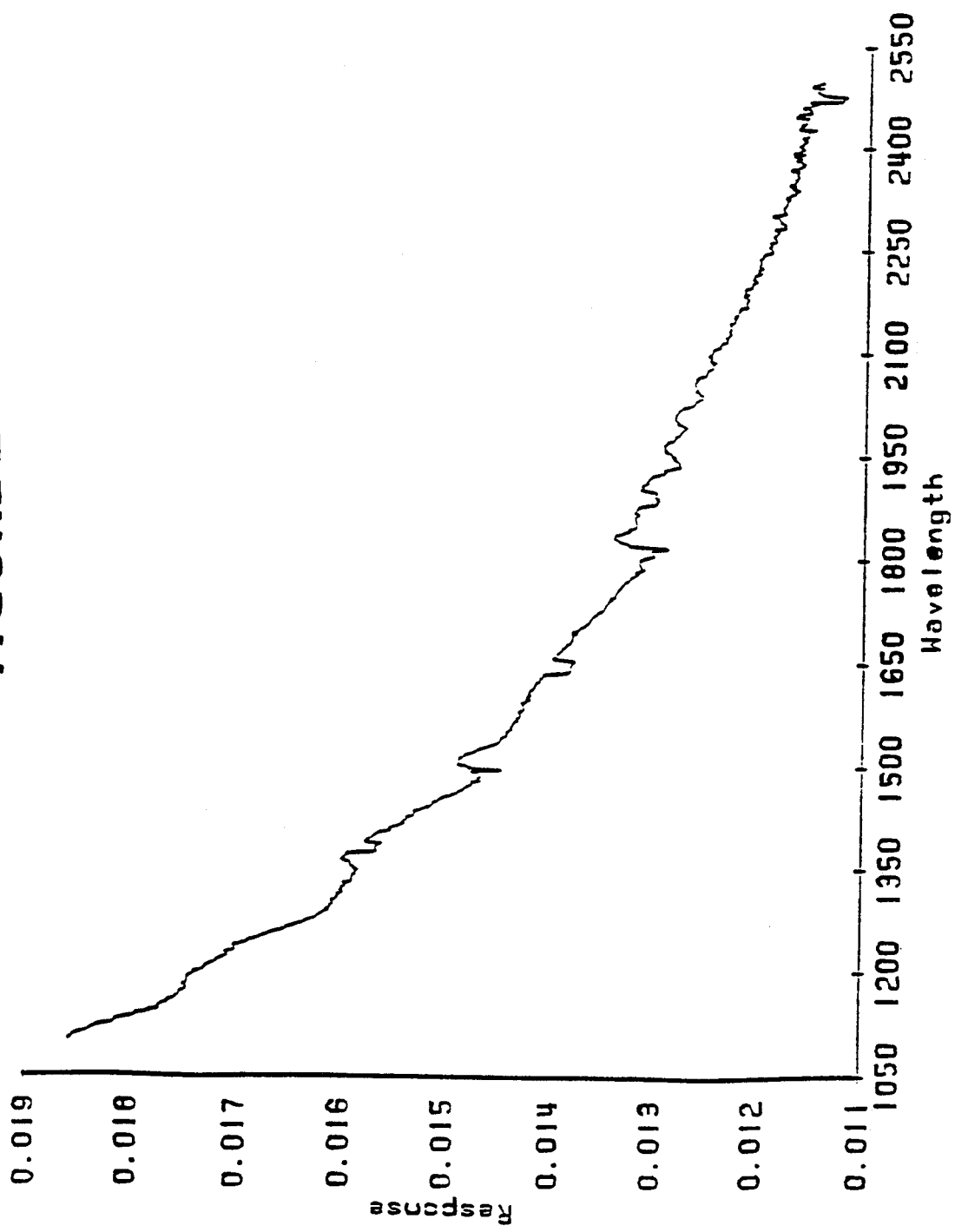

A zinc selenide etalon on a quartz substrate was selected as the stable etalon standard and was also analyzed at both source voltages and a simple spectral difference was used to estimate the instrument change. The resulting transfer function is shown in FIG. 2C. The transfer function can be obtained by any suitable mathematical approach such as using linear or nonlinear regression techniques to transform the wavelength and intensity axes, as will be appreciated by one skilled in the art. Using this transfer function, the polystyrene spectra acquired at 14.625 volts were modified to reflect the instrument change from the original spectra acquired at 15.06 volts.

Figure 2D:
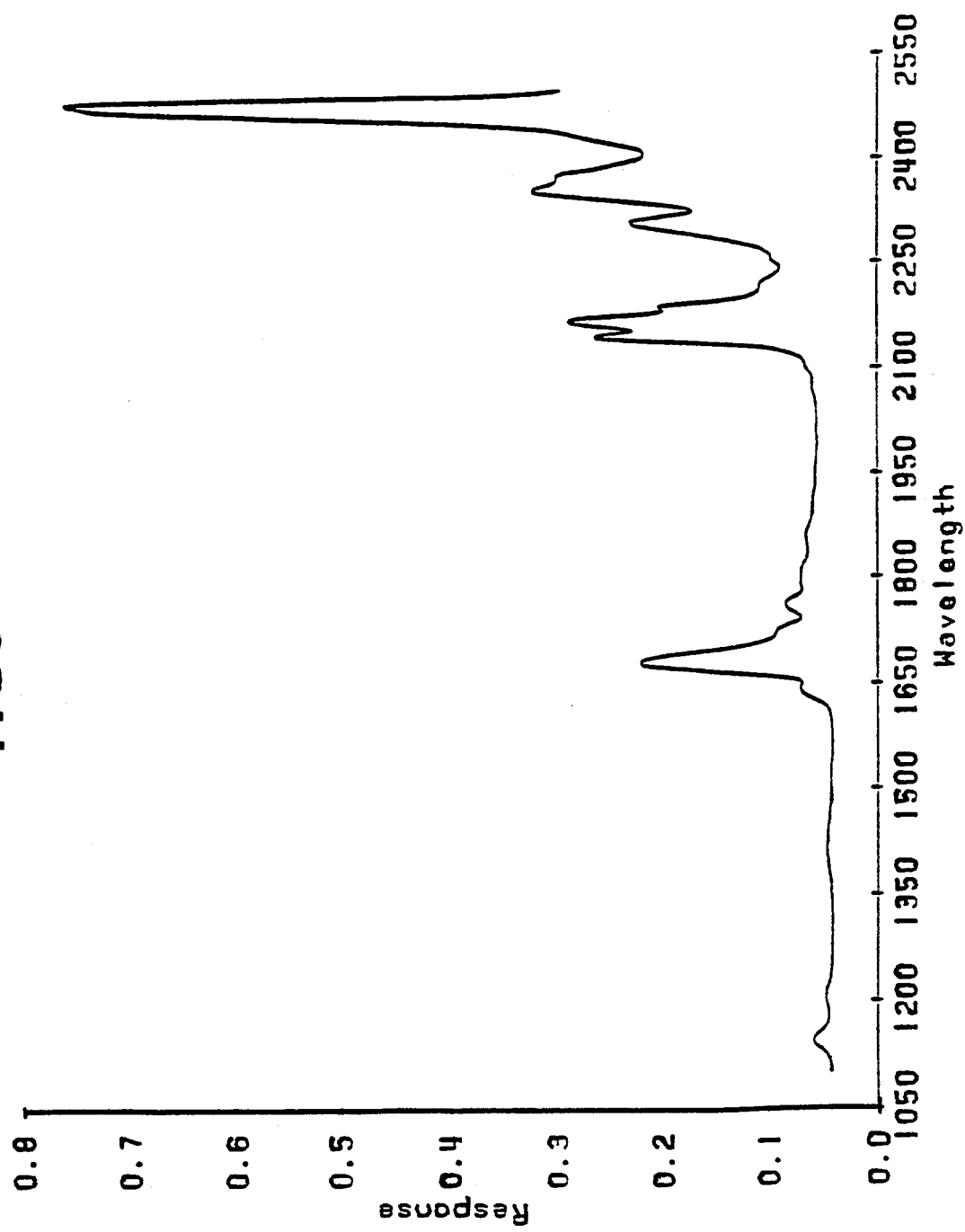

FIG. 2D shows the recalibrated spectrum acquired at 14.625 volts plotted with the polystyrene spectrum acquired with the source voltage at 15.06 volts. Because of the recalibration technique the recalibrated spectrum at 14.625 volts overlies the spectrum at 15.06 volts such that only a single line is visible. Comparing FIG. 2A with FIG. 2D demonstrates the effectiveness of using the etalon for instrument recalibration as the differences between the re-calibrated spectrum and the original spectrum is negligible.

The applicants have discovered that this calibration method can be used to recharacterize instrument response for light intensity as well as for wavelength. As will be appreciated, this is only one example of the recalibration method of the invention. More stable etalons and/or the use of multiple standards coupled with more sophisticated mathematical methods for deriving the transfer function should yield improved results.

Figure 3B:
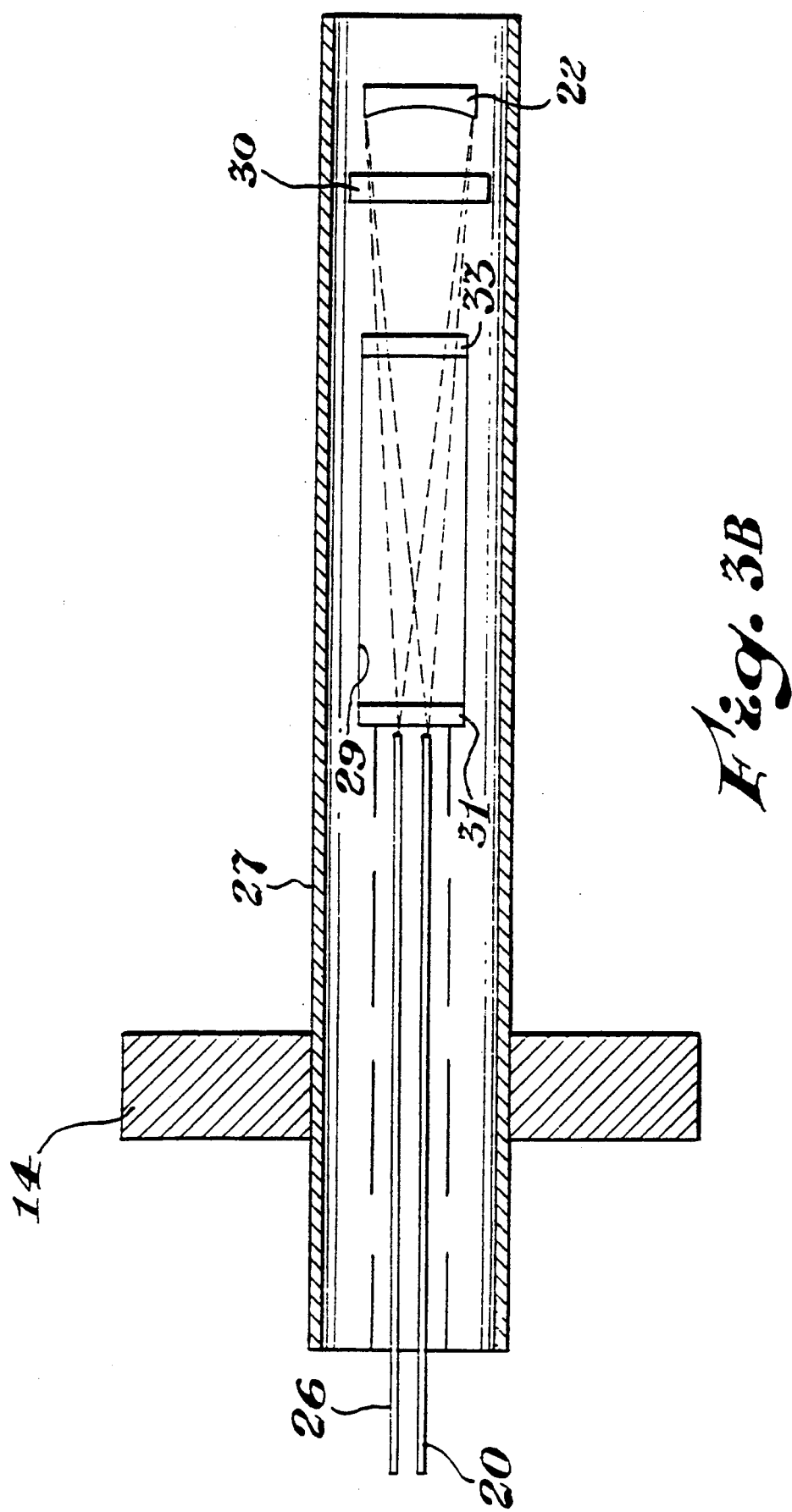
Figure 4A:
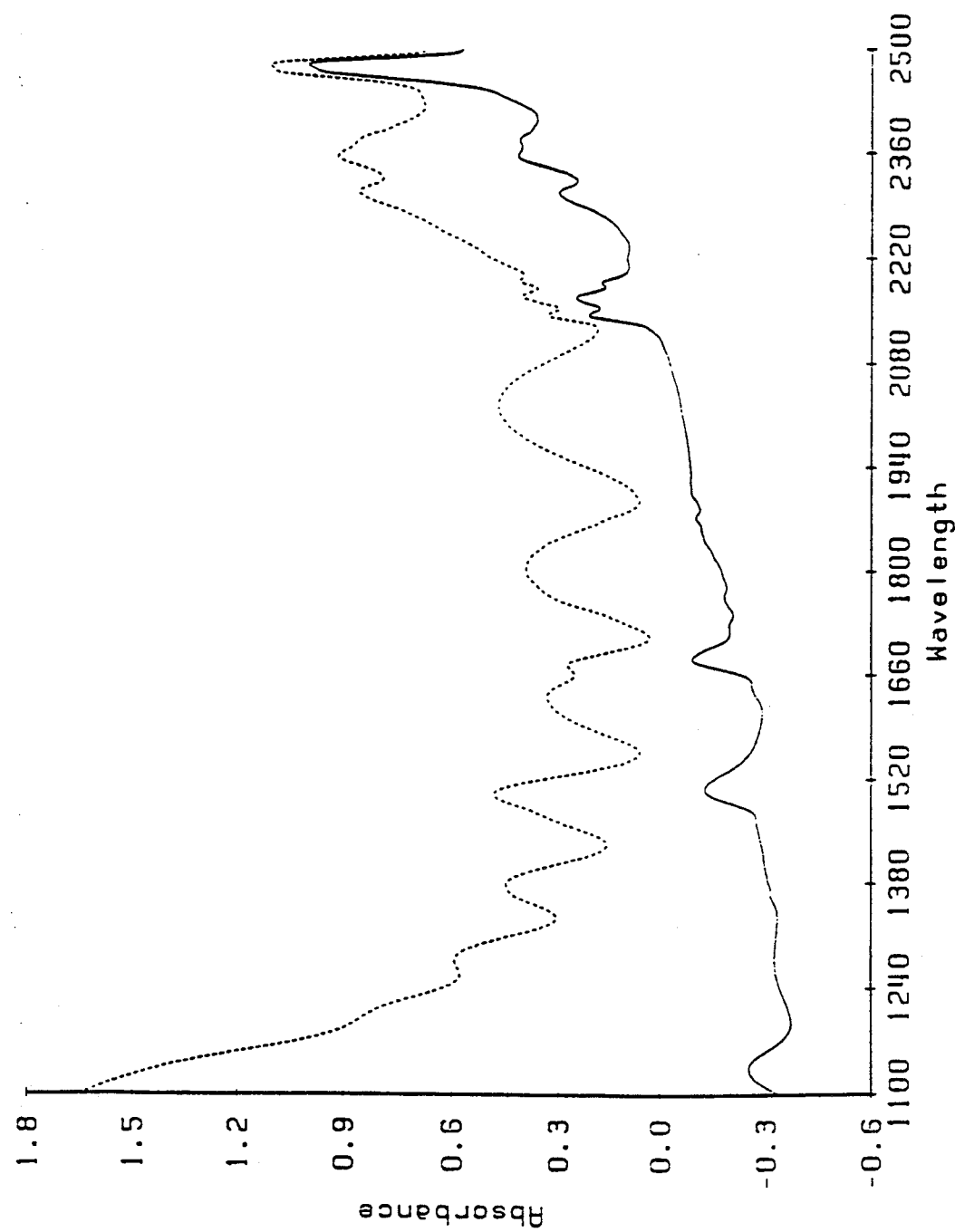
FIGS. 4A and 4B are graphs of the spectra illustrating the use of the system in situ.

FIGS. 3A and 3B show schematically the in situ recalibration system where the standard is in series with the sample being analyzed. For illustrative purposes the recalibration system is shown in conjunction with a chemical reactor 14 having a bath of chemicals 16 being mixed therein. Specifically, the light source fiber optic cable 20, reflector 22 and detector fiber optic cable 26 are housed in a protective sheath 27 submerged in bath 16. Sheath 27 is provided with an aperture 29 defined by windows 31 and 33 into which the bath can enter so as to create a sample between the light source and detector. The light source 2 from a spectrometer projects a light beam through the portion of bath 16 in aperture 29 via fiber optic cable 20. The light projected from cable 20 passes through bath 16, reflects from reflector 22 and is received by detector 8 via fiber optic cable 26. The resulting spectrum received by detector 8 is displayed on processor 10 which also controls the recharacterization of the spectrometer. This system allows the composition of the chemicals being mixed in the reactor 14 to be continuously monitored. While the illustrated embodiment includes a reflector, it will be appreciated that the reflector could be omitted and the detector fiber optic cable be placed in-line with the light source.

Figure 4B:
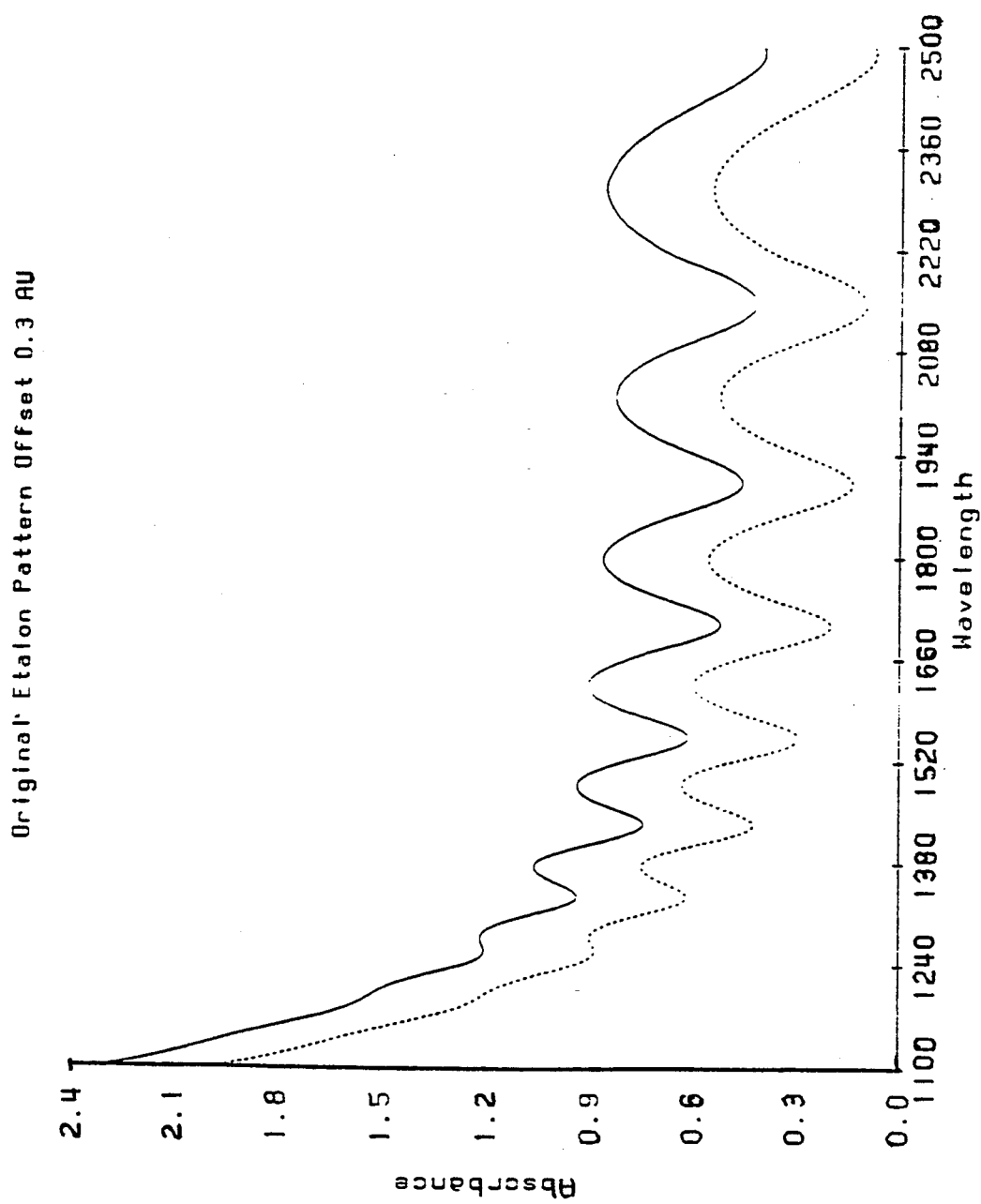

Periodically it is necessary to recalibrate the system. To do so, an etalon or other stable standard 7 is moved between the light source 2 and reflector 22. More preferably, the etalon standard 7 will be located between the light source 2 and the detector 8 as shown in FIG. 3A. Preferably, the etalon standard 7 can be moved into and out of the path of the light beam by any suitable automated transfer device controlled by computer 10. When the etalon is so positioned, the spectrum generated by detector 8 represents the combined effects of the etalon 7 and the composition of bath 16 as shown by the dotted line in FIG. 4A. To find the spectrum for the standard alone, the spectrum of the sample alone (solid line in FIG. 4A) is mathematically extracted from the spectrum of the sample and etalon. The extracted spectrum as shown by the dotted line in FIG. 4B is compared to the reference spectrum of the standard (solid line in FIG. 4B) and a transfer equation is used to recalibrate the optical instrument such that the extracted standard spectrum matches the reference standard spectrum as has previously been described. While one particular application of the invention has been described, it will be appreciated that the system can be used in any application which uses an optical monitoring instrument.

An additional application of the invention is to use etalons to calibrate the response of a plurality of instruments. This application is particularly useful in calibrating process instruments (i.e. instruments used at on site processes) to respond in the same manner as a lab instrument.

In this application, calibration equations are derived on the lab instrument using a set of known samples. These equations are used to estimate analytical results (e.g. protein content in wheat) from acquired spectra. Additionally, spectra for a plurality of etalons are acquired on the lab instrument to characterize that instrument's response. The etalon spectra are then acquired on each of the process instruments to be calibrated and a transfer function is developed for each process instrument. The transfer function for each process instrument is used on subsequent spectra acquired on that instrument to make the response substantially equivalent to that which would be produced by the lab instrument. Alternatively, the transfer function can be used to modify the calibration equations used to derive analytical results from the acquired spectra rather than modifying the spectra themselves.

While the invention has been described in particular detail with respect to the Figures, it is to be understood that the foregoing description is offered merely by way of example and that the invention is to be limited only by the appended claims.

What is claimed is:

1. An optical instrument which generates a variable response that can be calibrated in situ, comprising:
   a) means for generating a light beam;
   b) means for periodically exposing a sample to the light beam so that a sample spectrum can be generated;
   c) means for periodically exposing an etalon to the light beam so that an etalon spectrum can be generated;
   d) means for detecting the spectra generated by exposing the sample or etalon to the light beam;
   e) means for storing spectra; and
   f) means for comparing a current etalon spectrum to a previously generated etalon spectrum stored in the means for storing spectra, and for adjusting the instrument response to match the current etalon spectrum to the previously generated etalon spectrum.

2. The optical instrument according to claim 1, wherein a transfer function is used to adjust the instrument response to match the etalon spectrum of step (c) to the previously generated spectrum.

3. The instrument of claim 1 wherein the means for periodically exposing the etalon to the light beam is arranged in series with the means for exposing the sample to the light beam, so that a combined spectrum can be generated and wherein the instrument further comprises a means for extracting the etaton spectrum from the combined spectrum.

4. A method for recalibrating optical instruments of the type having a light source and a light detector for generating a response in the form of a spectrum characteristic of a sample, comprising the steps of:
   a) placing a sample between the light source and detector;
   b) generating a spectrum corresponding to the sample;
   c) placing an etalon between the light source and detector and in series with the sample;
   d) generating a combined spectrum of the etalon and the sample;
   e) extracting the spectrum for the sample from the combined spectrum for the etalon and sample to give a resulting spectrum of the etalon; and
   f) comparing the resulting spectrum with a reference spectrum and varying the instrument response so that the resulting spectrum matches the reference spectrum.

5. The method according to claim 4, wherein a transfer function is used to vary the instrument response.

6. The method of claim 4 further comprising repeating steps (c) through (f) for a plurality of etalons.

7. An optical instrument with simultaneous calibration of wavelength position and light intensity, comprising:
   a) means for storing a reference spectrum of a first etalon;
   b) means for generating a light beam;
   c) means for exposing a second etalon to the light beam, said second etalon being equivalent to the first etalon;
   c) means for detecting the light beam and for generating a corresponding spectrum representative of the second etalon; and
   d) means for comparing the reference spectrum to the corresponding spectrum; and
   e) means for adjusting the detected wavelength and intensity level characteristics of the instrument such that the corresponding spectrum matches the reference spectrum.

8. The optical instrument according to claim 7, wherein a transfer function is used to adjust the wavelength and intensity level characteristics of the instrument.

9. The instrument of claim 7 wherein the first etalon is the same as the second etalon and wherein the reference spectrum is generated by the optical instrument.

10. A method for simultaneously calibrating the wavelength position and light intensity of an optical instrument such as a spectrometer comprising the steps of:
    a) generating a light beam;
    b) intersecting the beam of light with an etalon;
    c) detecting the beam of light after intersection with the etalon and generating a first spectrum representing the spectrum of the etalon;
    d) intersecting the beam of light with an equivalent etalon and developing a second spectrum indicative of the current response of the instrument;
    e) comparing the second spectrum to the first spectrum and adjusting the wavelength and intensity characteristics of the optical instrument to match the second spectrum to the first spectrum.

11. The method according to claim 10, wherein a transfer function is used to adjust the wavelength and intensity characteristics of the optical instrument.

12. The method of claim 10 further comprising repeating steps (b) through (e) for a plurality of etalons.

13. In an optical instrument which measures light intensity at various wavelengths, said instrument having a means for generating a light beam, a means for exposing a sample to the light beam so that a sample spectrum can be generated, a means for exposing an etalon to the light beam so that an etalon spectrum can be generated, a means for detecting the intensity of the light beam at various wavelengths after passing through the sample and/or etalon and a means for using the etalon spectrum for calibrating the wavelength of said optical instrument, the improvement comprising: arranging in series the means for exposing the sample to the light beam and the means for exposing the etalon to the light beam so that a combined sample and etalon spectrum can be generated.

14. The instrument of claim 13 further comprising a means for extracting the etalon spectrum from the combined sample and etalon spectrum.

15. The instrument of claim 14 further comprising a means for using the etalon spectrum for calibrating the light intensity detected by the instrument.

16. In an optical instrument which measures light intensity at various wavelengths, said instrument having a means for generating a light beam, a means for exposing a sample to the light beam so that a sample spectrum can be generated, a means for exposing an etalon to the light beam so that an etalon spectrum can be generated, a means for detecting the intensity of the light beam at various wavelengths after passing through the sample and/or etalon and a means for using the etalon spectrum for calibrating the wavelength of said optical instrument, the improvement comprising: a means for using the etalon spectrum for calibrating the light intensity detected by the instrument.

17. In a method for calibrating an optical instrument having a means for generating a light beam, a means for generating spectra by exposing materials to the light beam and a means for detecting the spectrum by measuring the light intensity at various wavelengths, said method being of the type wherein an etalon is exposed to the light beam and the resulting spectrum is used to adjust the frequency response of the instrument, the improvement comprising:

generating a combined sample and etalon spectrum; and extracting the etalon spectrum from the combined spectrum.

18. The method of claim 17 wherein the extracted etalon spectrum is used to adjust the intensity and/or frequency response of the instrument.

19. The method of claim 18 wherein the extracted etalon spectrum is used to adjust the intensity and frequency response of the instrument.

20. In a method for calibrating an optical instrument having a means for generating a light beam, a means for generating spectra by exposing materials to the light beam and a means for detecting the spectrum by measuring the light intensity at various wavelengths, said method being of the type wherein an etalon is exposed to the light beam and the resulting spectrum is used to adjust the frequency response of the instrument, the improvement comprising: using the spectrum resulting from exposing the etalon to the light beam to adjust the intensity response of the instrument.

* * * * *